United States Patent [19]

Eck et al.

[11] 4,107,002
[45] Aug. 15, 1978

[54] PROCESS FOR THE PURIFICATION OF CRUDE ACETIC ANHYDRIDE

[75] Inventors: Herbert Eck; Elmar Bethe; Hans Schwarzbauer; Hellmuth Spes; Klaus Kaiser, all of Burghausen, Fed. Rep. of Germany

[73] Assignee: Wacker-Chemie GmbH, Munich, Fed. Rep. of Germany

[21] Appl. No.: 654,309

[22] Filed: Feb. 2, 1976

[30] Foreign Application Priority Data

Feb. 10, 1975 [DE] Fed. Rep. of Germany ....... 2505471

[51] Int. Cl.² .................. B01D 1/00; B01D 3/14; C07C 53/12
[52] U.S. Cl. .................. 203/75; 203/DIG. 19; 260/546; 202/155
[58] Field of Search .................. 203/73, 77, 80, 91, 203/72, 82, 75, 16, DIG. 19, 99; 260/545 R, 546–549, 541; 202/155

[56] References Cited

U.S. PATENT DOCUMENTS

| 2,159,146 | 5/1939 | Guinot | 203/16 |
|---|---|---|---|
| 2,504,195 | 4/1950 | Hall et al. | 260/546 X |
| 2,670,355 | 2/1954 | Barsky et al. | 203/75 |
| 2,688,635 | 9/1954 | Eberts et al. | 260/547 |
| 2,703,309 | 3/1955 | Painter | 260/546 X |
| 2,895,886 | 7/1959 | Schneider | 203/72 |
| 3,392,091 | 7/1968 | Hohenschutz | 203/73 |
| 3,644,179 | 2/1972 | Knoer et al. | 203/72 |

*Primary Examiner*—Wilbur L. Bascomb, Jr.
*Attorney, Agent, or Firm*—Allison C. Collard

[57] ABSTRACT

A process for the purification of crude acetic anhydride by continuous fractional distillation, which comprises first introducing the anhydride into an evaporator, thereafter removing from the evaporator the non-distillable components contained in the crude anhydride, then introducing the distillable components of the anhydride in vapor form into about the central section of a fractionating column, withdrawing from the top of the column the low boiling components together with acetic acid, withdrawing near the bottom of the column a high-percentage of pure acetic anhydride, and separating from the sump of the column up to about 8% by weight based on the initial amount of crude acetic anhydride and returning the same to the evaporator.

5 Claims, 4 Drawing Figures

PROCESS FOR THE PURIFICATION OF CRUDE ACETIC ANHYDRIDE

The present invention relates to a process for the purification of crude anhydride by continuous fractional distillation.

The large-scale industrial production of acetic anhydride by known processes, for example, the thermal splitting of acetic acid or acetone or the oxidation of acetaldehyde yields a crude product. This is subsequently purified by fractional distillation.

The degree of purity of acetic anhydride can be measured by its percentage content of acetic anhydride, by its so-called permanganate number, and by its color number. The permanganate number is a measure of the content of permanganate-reducing substances and should desirably be as low as possible. The color number, which is determined by the APHA test according to DIN 53 409, is based on a visual color comparison between the solution to be examined and a standard solution containing platinum and cobalt. This number also should desirably be as low as possible.

Both discontinuous and continuous methods have been used for the purification of crude acetic anhydride by fractional distillation, but the discontinuous method has generally produced purer products than those resulting from the continuous method. The discontinuous method has the disadvantage, however, of requiring a large expenditure on apparatus, because it involves three separate stages. The impurities with low boiling points are removed in the first stage. During the second stage, a large amount of acetic acid and the majority of the low boiling, reducing substances are removed, the reducing substances being the ones that impair the permanganate number. The main fraction, that is the required acetic anhydride, is distilled off in the third stage, but if this stage is continued for too long, the permanganate number and the color number of the distillate will start to increase due to the presence of higher boiling impurities.

Various processes are known for carrying out the purification of crude anhydride by the continuous distillation method. One process involves the use of three columns, corresponding to the three stages of the discontinuous method, and thus also requires a large expenditure on apparatus. Attempts have been made to reduce the number of columns, either by combining the first two stages or by using only one column (cf. Ullmann's Encyklopädie der technischen Chemie vol. 6, 3rd ed (1955), pp 808 ff). In these attempts, the higher boiling impurities consisting, as mentioned above, of the color and permanganate numbers impairing substances are removed as part of the distillation residue, or sump, which also contains non-distillable coal-like or tar-like substances and residual acetic anhydride. The residual acetic anhydride can be extracted, if desired, by means of an additional process stage such, for example, as thin layer evaporation. However, these continuous processes using one or two fractionation stages do not yield products of satisfactory purity.

It is the object of the present invention to provide a simple process for the continuous purification of crude acetic anhydride, which avoids the shortcomings of the known processes and permits one to obtain a completely satisfactory product, as well as concerns contents in anhydride, as color and permanganate numbers, by the use of a single column.

The process according to the invention comprises separating the crude acetic anhydride, by means of evaporation in a first evaporator, into a part consisting of gaseous distillable components and another part consisting substantially of non-gaseous non-distillable components which are removed; the first part from the evaporator is passed into the central section of a fractionating column and fractionated therein, in such a manner that a fraction consisting substantially of components having a boiling point below that of acetic anhydride is removed from the column at the top. At a point near the bottom of the column, a fraction consisting substantially of pure acetic anhydride, is withdrawn in liquid state. Moreover, from the sump of the column a liquid residue consisting substantially of acetic anhydride and accumulated impurities is removed, part of the residue being returned to the first evaporator, the remainder of the liquid residue being passed to a second evaporator, the resulting gaseous residue being used for heating the fractionating column.

The present process yields, by the use of only one fractionating column in a continuous process, a product consisting of acetic anhydride of satisfactory purity with regard to both its permanganate number and its color number. In this process, the non-distillable components of the crude acetic anhydride are removed prior to the fractionation and this prevents the formation of cracked products from such components, which generally adversely affect the color and permanganate numbers. The purity of the product obtained by this process generally exceeds that obtained by other continuous processes using one or two fractionating columns or using an especially constructed selective fractionating column.

The process according to the invention may be carried out either under atmospheric pressure or under sub-atmospheric pressure. For economical reasons, the use of sub-atmospheric pressure is generally preferred. This has the advantage that there is a decreased likelihood of soiling of the apparatus, and particularly of the first evaporator, which would require the use of expensive cleaning processes. Advantageously, a pressure above 20 mm Hg measured at the vacuum pump should be used since a further pressure reduction would render it difficult to condense the lower-boiling components after their removal from the fractionating column. There would also be a danger of glacial acetic acid crystallizing out and blocking the pipes.

The invention will now be described in greater detail, by way of illustration only, and not of limitation; also the novel process is compared with known processes for the continuous purification of crude acetic anhydride, with reference to the accompanying drawings in which.

Figure 1:
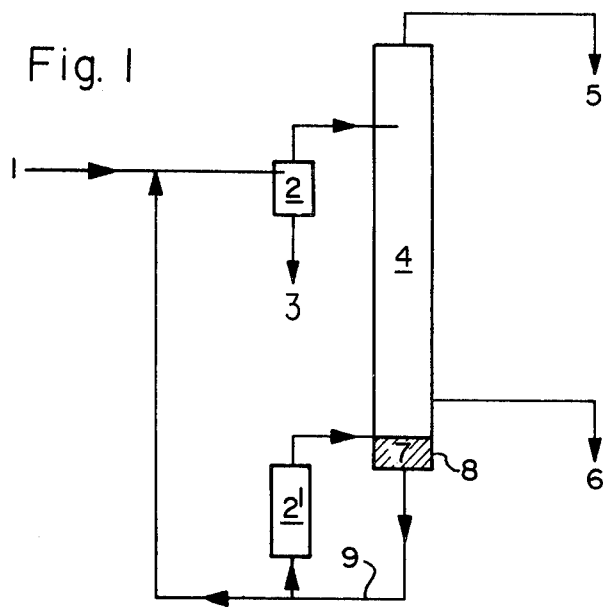
FIG. 1 is a schematic representation of an apparatus used for carrying out the process of the invention.

In the process of the invention as described in Example 1 and illustrated in FIG. 1, crude acetic anhydride is introduced through a pipeline 1 into a first evaporator 2, which is advantageously an evaporator designed for circulation and in the following, called "circulation evaporator". The crude acetic anhydride is here evaporated to separate off the non-distillable components which leave the evaporator 2, in non-gaseous form, through outlet 3. This initial separation of the non-distillable components from the crude acetic anhydride prior to its fractionation is an essential feature of the present process. The distillable components of the crude acetic anhydride leave the evaporator 2 in gaseous form and are passed into a substantially central section of a fractionating column 4, where they are fractionated. A first fraction consisting substantially of components having a boiling point below that of acetic anhydride (mainly acetic acid, acetone and methyl acetate) is drawn off from the top of the column through escape line 5. A second fraction, in liquid form, consisting substantially of high percentages acetic anhydride, is drawn off from the lower part of the column, but above the sump of column 4, through outlet line 6. A liquid residue 7, consisting substantially of crude acetic anhydride and some components having a boiling point higher than that of acetic anhydride as well as of accumulated impurities, collects in the sump 8 of column 4. This liquid residue 7 is removed from the sump 8 and a part of it is passed through a line 9, to a second evaporator 2', which is also advantageously a circulating evaporator, where it is evaporated and then returned to column 4 at a point just above sump 8. This liquid residue in gaseous form serves to provide the heat required for fractionation. Part of liquid residue 7 is returned to first evaporator 2, in order to prevent a build-up of distillation residue in second evaporator 2'. The amount returned to first evaporator 2 is advantageously up to 8% by weight, and preferably from 0.5 to 4% by weight, based on the initial amount of crude acetic anhydride.

The fraction obtained from outlet line 6 generally has an acetic anhydride content of more than 98%, with a color number of less than 5 and a permanganate number of less than 10, which correspond to the highest required purity values.

By our own investigations, we have shown that with a single column and a single evaporator for heating the same, but without prior separation of the non-distillable portions before introduction of the product into the column, the resulting acetic anhydride had an unsatisfactory color number and permanganate number as more fully described in the example below.

Figure 2:
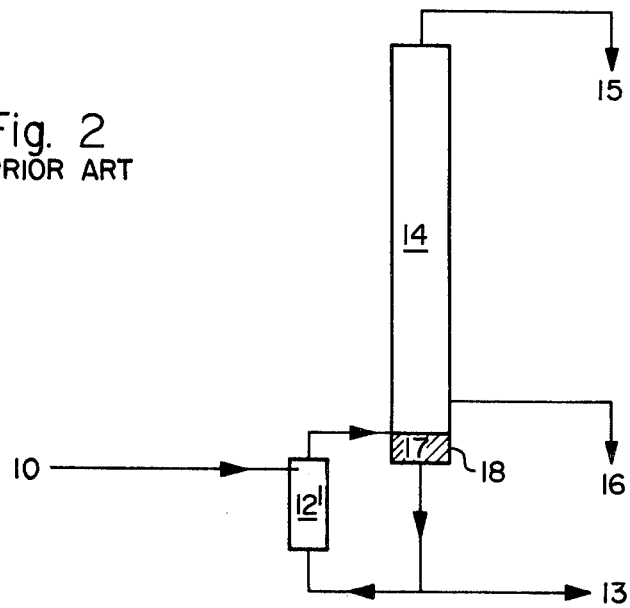
FIG. 2 is a schematic representation of an apparatus, including a single fractionating column, used for carrying out the process according to Ullman (loc. cit.)

In the process according to Ullman (loc. cit.) illustrated by FIG. 2, crude acetic anhydride is introduced through line 10 directly into a single evaporator 12' and then passed, in gaseous state, to sump 18 at the bottom of a column 14. This gaseous crude acetic anhydride provides the heat necessary for fractionation. A fraction consisting substantially of components having a boiling point lower than that of acetic anhydride is removed through outlet line 15 and a fraction consisting substantially of acetic anhydride is removed through outlet line 16. A liquid residue 17, comprising non-distillable components, collects in sump 18 of column 14, and is partially returned to evaporator 12' and partially removed through outline line 13.

Although the fraction obtained from outlet 16 generally has an acetic anhydride content of at least 98%, it tends to be yellowish with a color number of 15 to 20. However, it generally has a permanganate number of 20 to 40. These values are unsatisfactory for many purposes.

Figure 3:
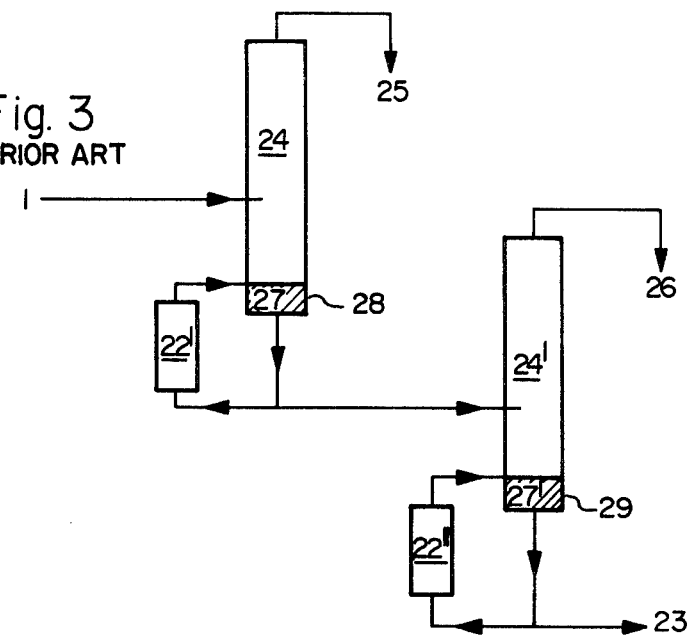
FIG. 3 is a schematic representation of an apparatus used for carrying out a process using two fractionating columns, according to the prior art.

In a known two-column process illustrated by FIG. 3, crude acetic anhydride is introduced through line 21 directly into a first fractionating column 24. A fraction consisting substantially of the components having a boiling point lower than that of acetic anhydride is removed together with acetic acid from the top of column 24 through line 25. The remainder of the crude acetic anhydride collects in sump 28 of column 24 as a liquid residue 27. Part of this liquid residue 27 is passed to a first evaporator 22' and then returned to the column to provide the heat required for fractionation, and the remainder is passed to a second fractionating column 24'. A fraction consisting substantially of pure acetic anhydride is removed from the top of this second column 24' through outlet 26. The remaining components collect in sump 29 of this second column 24' as a liquid residue 27', part of which (non-distilled components) is removed through outlet 23 and part of which is returned to the column 24' via a second evaporator 22" in order to provide the heat required for the second fractionation stage.

In an alternative two-column process (FIG. 4), the first fractionation stage is carried out in column 34 as described with reference to FIG. 3. The liquid residue 37 is passed via the second evaporator 32" to the second column 34'. A fraction consisting substantially of further components having a boiling point lower than that of acetic anhydride is removed from the top of the second column 34' through outlet 38, and a fraction consisting substantially of acetic anhydride is removed from lower down the second column 34' through outlet 36. The remaining components collect as a liquid residue 37' as described with reference to FIG. 3.

The fraction obtained from outlet 26 and 36, respectively in each of these two-column processes generally has an acetic anhydride content of at least 98% but is yellowish. It generally has a color number of 15 to 25 and a permanganate number of 10 to 40.

By the essential feature of the present invention which consists of separating out the non-distillable components of crude acetic anhydride before the anhydride is passed into the fractionating column, the formation of cracked products is prevented to a high degree, which products normally impair the permanganate and color numbers. As a consequence, pure acetic anhydride can be withdrawn as a liquid from the column above the sump which is practically free of residue.

The process according to the invention renders it possible to obtain by purification of crude acetic anhydride, a final product which meets the highest specifications of purity, by a continuous distillation process using a much simpler apparatus. The effect also surpasses the one obtained by use of two columns, even when one of them is designed especially for selective operation.

Various examples have been carried out to illustrate the process of the invention and to compare it with prior art processes. Examples 1 illustrates the process of the invention and uses apparatus as shown in FIG. 1. Examples 2 to 4 are for comparison purposes and use the apparatuses shown in FIGS. 2 to 4, respectively. The fractionating column or columns used in the examples were each 20 cm in diameter and 600 cm in height and were filled with "Berlsätteln" (a filling material with a large surface area). The permanganate numbers and color numbers of the products of the examples were determined as described below.

(a) Permanganate number 5 ml of acetic anhydride were added drop-wise to 50 ml of a 5% aqueous sulphuric acid solution. The resulting solution was titrated at 20° – 25° C with a 1 : 1000 aqueous solution of potassium permanganate (1 g KmnO$_4$/liter H$_2$O) until a red coloring lasting for at least 1 minute was obtained. The permanganate number is given by the number of milliliters of permanganate consumed multiplied by 20 (to give a comsumption based on 100 ml).

(b) Color number

The color number was determined by the APHA test according to DIN 53 409. This method is based on a visual comparison of the liquid under test with various standardized solutions containing platinum and cobalt. The color number is given by the platinum content in mg/l of the standardized solution that most nearly corresponds in color with the liquid under test.

A stock solution was prepared by dissolving 1.246 g of K$_2$PtCl$_6$ (corresponding to 500 mg Pt) and 1 g of CoCl$_2$.6H$_2$O (corresponding to 250 mg Co) in 100 ml of concentrated HCl and diluting the solution of 1000 ml with distilled water. This stock solution corresponds to APHA 500 (500 mg Pt/l).

Five standardized solutions were prepared from this stock solution by taking, respectively, 1 ml, 2 ml, 3 ml, 4 ml and 5 ml of the stock solution (containing respectively 0.5 mg, 1.0 mg, 1.5 mg, 2.0 mg of Pt) and diluting each portion to 100 ml with distilled water. The resulting standardized solutions had the color number APHA 5, APHA 10, APHA 15, APHA 20 and APHA 25, respectively.

The test tubes used for the comparison of the liquid under test with the standard solutions had an internal diameter of about 20 mm, a filling height of about 310 mm, and a filling volume of about 100 ml.

The standard solutions were closed with ground-in stoppers.

EXAMPLE 1, illustrated in FIG. 1

100 Kg/h of crude acetic anhydride, having an acetic anhydride content of 89.5% by weight and a permanganate number of 290, were introduced into a first circulating evaporator 2. 3 kg/h of exhaust anhydride from the sump 8 of the column was also introduced into first evaporator 2. 1 kg/h of non-distillable components were removed from evaporator 2 via outlet 3. 102 kg/h of gaseous distillable components were passed, at a pressure of 140 mm Hg (as measured by a vacuum pump), from evaporator 2 into fractionating column 4 at a point 450 cm from the bottom of the column. 20 kg/h of distillate were removed through outlet 5 at a reflux ratio of 10 : 1. 79 kg/h of purified acetic anhydride were removed as a liquid through outlet 6 (150 cm from the bottom of the column). This product had a purity of 98.5%, a permanganate number of 6-8 and a color number of less than APHA 5. After 1800 operating hours, there was no appreciable soiling in either of the evaporators 2 and 2' the residue content was less than 0.1%.

EXAMPLE 2, (comparison example with simple column apparatus according to Ullmann and illustrated by FIG. 2)

100 kg/h of crude acetic anhydride (having the same properties as that used in Example 1) were introduced not into the circulating evaporator 12', but directly into sump 18 of column 14. 1 kg/h of residue was removed from the sump through outlet 13. 20 kg/h of distillate were removed through outlet 15 and 79 kg/h of purified acetic anhydride were removed through outlet 16. The product had a purity of 98.5% but a permanganate number of 20 – 40 and a color number of APHA 15 – 20.

EXAMPLE 3, (comparison example with two-column apparatus as known in the art and illustrated in FIG. 3)

100 kg/h of crude acetic anhydride, having an acetic anhydride content of 90% by weight and a permanganate number of 300, were introduced into first column 24 through inlet 21. 16 kg/h of distillate were removed from the top of first column 24 through outlet 25 at a reflux ratio of 7:1. The liquid from the sump 28 of the column 24 was passed into the second column 24' approximately at the center and 1 kg/h of residue was removed from sump 29 of second column 24' through outlet 23. 83 kg/h of purified acetic anhydride was obtained as a distillate in vapor form from outlet 26. This had an acetic anhydride content of 98.5% by weight, a permanganate number of 40 and a color number of APHA 20 – 35.

Figure 4:
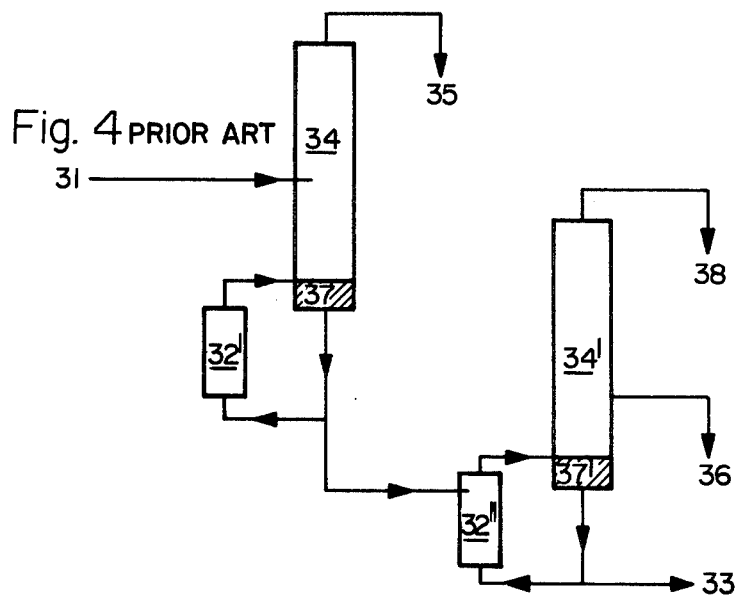
FIG. 4 is a schematic representation of an alternative apparatus containing two fractionating columns, according to the prior art.

EXAMPLE 4, (comparison example with two-column apparatus illustrated in FIG. 4)

Fractionation in the first column 34 was carried out as in Example 3. However, 4 kg/h of distillate was removed from the top of second column 34' through outlet 38 at a reflux ratio of 20 : 1. 79 kg/h of purified acetic anhydride was removed through outlet 36 in a gaseous state. This had an acetic anhydride content of 98.5% by weight, a permanganate number of 10 – 20 and a color number of PAPHA 15 – 20.

While only a few embodiments have been shown and described it will be obvious to those skilled in the art that many changes and modifications may be made thereunto without departing from the spirit and scope of the invention.

What is claimed is:

1. A process for the purification of crude acetic anhydride, which contains at least 89.5% by weight of acetic anhydride, by continuous fractional distillation to obtain substantially pure acetic anhydride having a content of above 98% by weight of acetic anhydride and having a permanganate number of less than 10 and a color number of less than 5, the steps comprising:

introducing the crude acetic anhydride into a first evaporator and separating the crude acetic anhydride into vaporous distillable and non-vaporous non-distillable components;

thereafter removing the non-distillable components from the first evaporator and from the purification process and then introducing the vaporous distillable components into about the central section of a fractional distillation column and fractionally distilling it therein;

withdrawing from the top of the column components having a boiling point below that of acetic anhydride, withdrawing from near the bottom of the column substantially pure acetic anhydride having a content of above 98% by weight of acetic anhydride and having a permanganate number of less than 10 and a color number of less than 5, and removing from the sump of the column a liquid residue consisting substantially of crude acetic anhydride and accumulated impurities having a boiling point higher than that of acetic anhydride; said fractional distillation being the sole fractional distillation of said pure acetic anhydride and returning up to about 8% by weight of the liquid residue to said first evaporator, based upon the initial amount of crude acetic anhydride introduced into the first evaporator.

2. The process according to claim 1, wherein the amount of the liquid residue returned to the first evaporator is from 0.5 to 4% by weight, based on the initial amount of crude acetic anhydride introduced into the first evaporator.

3. The process according to claim 1, wherein said entire process is carried out under sub-atmospheric pressure.

4. The process according to claim 1, wherein said entire process is carried out under a pressure of not less than 20 mm Hg.

5. The process according to claim 1 additionally including the steps of introducing the remainder of the liquid residue not returned to the first evaporator into a second evaporator and converting it into a vaporous state and thereafter introducing the residue in a vaporous state into the fractional distillation column at a point below the point of removal of said substantially pure acetic anhydride.

* * * * *

UNITED STATES PATENT AND TRADEMARK OFFICE
CERTIFICATE OF CORRECTION

PATENT NO. : 4,107,002
DATED : August 15, 1978
INVENTOR(S) : Herbert Eck et al.

It is certified that error appears in the above-identified patent and that said Letters Patent are hereby corrected as shown below:

Column 5, line 27, after "2.0 mg", insert -- and 2.5 mg --

Signed and Sealed this

Thirteenth Day of March 1979

[SEAL]

Attest:

RUTH C. MASON
Attesting Officer

DONALD W. BANNER
Commissioner of Patents and Trademarks